(12) United States Patent
Olsson et al.

(10) Patent No.: US 11,448,600 B1
(45) Date of Patent: Sep. 20, 2022

(54) MULTI-CAMERA PIPE INSPECTION APPARATUS, SYSTEMS AND METHODS

(71) Applicant: SeeScan, Inc., San Diego, CA (US)

(72) Inventors: Mark S. Olsson, La Jolla, CA (US); Eric M. Chapman, Lake Tapps, WA (US); Nicholas A. Smith, Chula Vista, CA (US); Alexander L. Warren, San Diego, CA (US)

(73) Assignee: SEESCAN, INC., San Diego, CA (US)

( * ) Notice: Subject to any disclaimer, the term of this patent is extended or adjusted under 35 U.S.C. 154(b) by 210 days.

(21) Appl. No.: 15/806,219

(22) Filed: Nov. 7, 2017

Related U.S. Application Data

(63) Continuation of application No. 13/913,485, filed on Jun. 9, 2013, now Pat. No. 9,835,564.

(60) Provisional application No. 61/778,085, filed on Mar. 12, 2013, provisional application No. 61/657,721, filed on Jun. 8, 2012.

(51) Int. Cl.
| | |
|---|---|
| *H04N 5/00* | (2011.01) |
| *G02B 23/24* | (2006.01) |
| *A61B 1/05* | (2006.01) |
| *A61B 1/00* | (2006.01) |
| *G01N 21/88* | (2006.01) |
| *H04N 5/225* | (2006.01) |
| *G02B 13/06* | (2006.01) |

(52) U.S. Cl.
CPC ..... *G01N 21/8803* (2013.01); *A61B 1/00193* (2013.01); *A61B 1/05* (2013.01); *G02B 13/06* (2013.01); *G02B 23/243* (2013.01); *G02B 23/2484* (2013.01); *H04N 5/2252* (2013.01); *H04N 5/2258* (2013.01); *H04N 2005/2255* (2013.01)

(58) Field of Classification Search
None
See application file for complete search history.

(56) References Cited

U.S. PATENT DOCUMENTS

| | | | |
|---|---|---|---|
| 5,800,341 A | 9/1998 | McKenna et al. | |
| 6,545,704 B1 | 4/2003 | Olsson et al. | |
| 2005/0275725 A1* | 12/2005 | Olsson | G03B 37/005 |
| | | | 348/207.99 |
| 2006/0152589 A1* | 7/2006 | Morrison | G06K 9/209 |
| | | | 348/208.1 |
| 2009/0326321 A1 | 12/2009 | Jacobsen et al. | |

FOREIGN PATENT DOCUMENTS

| | | |
|---|---|---|
| WO | 2013/116394 | 8/2013 |

OTHER PUBLICATIONS

International Searching Authority, "Written Opinion of the International Searching Authority" for PCT Patent Application No. PCT/US2013/045000, dated Feb. 6, 2015, European Patent Office, Munich.

* cited by examiner

*Primary Examiner* — Edemio Navas, Jr.
(74) *Attorney, Agent, or Firm* — Steven C. Tietsworth, Esq.; Michael J. Pennington, Esq.

(57) ABSTRACT

Camera heads including multiple imaging elements with overlapping Fields of View (FOV) for inspecting pipes or cavities are disclosed.

10 Claims, 9 Drawing Sheets

MULTI-CAMERA PIPE INSPECTION APPARATUS, SYSTEMS AND METHODS

CROSS-REFERENCE TO RELATED APPLICATIONS

This application is a continuation of co-pending U.S. patent application Ser. No. 13/913,485, filed on Jun. 9, 2013, entitled MULTI-CAMERA PIPE INSPECTION APPARATUS, SYSTEMS AND METHODS, which claims priority under 35 U.S.C. § 119(e) to U.S. Provisional Patent Application Ser. No. 61/778,085, filed on Mar. 12, 2013, entitled MULTI-CAMERA PIPE INSPECTION APPARATUS, SYSTEMS AND METHODS, and to U.S. Provisional Patent Application Ser. No. 61/657,721, filed on Jun. 8, 2012, entitled MULTI-CAMERA PIPE INSPECTION APPARATUS, SYSTEMS AND METHODS. The content of each of these applications is incorporated by reference herein in its entirety for all purposes.

FIELD

This disclosure relates generally to apparatus, systems, and methods for visually inspecting the interior of pipes and other conduits or voids. More specifically, but not exclusively, the disclosure relates to apparatus and systems for providing images or video of the inside of a pipe based on data received from a plurality of imaging sensors.

BACKGROUND

Pipes are often prone to obstructions through a variety of mechanical, structural, and/or environmental factors, such as, for example, invasion by tree roots and/or other vegetation, build-up and corrosion, as well as other blockages. Various devices and methods for visualizing the interior of a pipe are known in the art. Current pipe inspection systems typically include a single imaging element coupled to the end of a push-cable to inspect the interior of pipes, conduits, and other voids. The images acquired during the pipe inspection are then viewed on a display device. However, current systems are limited in their ability to provide sufficient imaging and other data to the user, as well as to cover wide fields of view.

Accordingly, there is a need in the art to address the above-described problems, as well as other problems.

SUMMARY

This disclosure relates generally to apparatus, systems, and methods for visually inspecting the interior of pipes and other conduits or voids. More specifically, but not exclusively, the disclosure relates to apparatus and systems for providing images or video of the inside of a pipe based on data received from a plurality of imaging sensors.

For example, in one aspect, the disclosure relates to a camera head including an array of two or more imaging elements with overlapping Fields of View (FOV). The camera head may be fixedly or removably coupled to the end of a push-cable to allow inspect the interior of a pipe, conduit, and the like by being pushed into the pipe. The camera head may include one or more light source elements, such as LEDs for providing illumination in dimly lit inspection sites, such as the interior of underground pipes. The imaging elements and LEDs may be used in conjunction with a remote display device, such as an LCD panel or monitor in proximity to an operator, to display the interior of a pipe or other cavity. The display device may be part of a camera controller device or other display or data storage device, such as a notebook computer, tablet, smart phone, and the like.

In another aspect, the imaging elements and light source elements may be automatically controlled and/or manually controlled by the operator. For example, automatic control may be used to provide an image or video signal from one or more of the imaging elements based on an orientation of the camera within the pipe or cavity. Control signals may be provided from an orientation sensor such as an accelerometer or other orientation sensor. Manual control may be used to allow an operator to select one or more of the imaging elements and/or one or more of the LEDs for viewing the interior of the pipe or other cavity, such as by a switch, button, or other user input mechanism. The LEDs may be individually controlled, such as turning one or more LEDs on or off to reduce heat in the camera head. The LEDs may additionally be used individually to provide various shadow patterns, which may be useful for diagnosing an inspection area. Images or video acquired from the imaging elements may be processed to provide a 3-dimensional view of the interior of the pipe or other cavity. Images or video may be captured from multiple imaging sensors and processed in an electronic circuit of a camera apparatus, such as within a camera head, to generate an output signal including output images or video based on imaging data received from a plurality of the imaging sensors. The output signal may include a digitally synthesized articulation of the camera head based on data received by the plurality of imaging sensors.

In another aspect, the disclosure relates to image processing methods used in a multi-camera pipe inspection system. Such methods may include, for example, generating a new image based on the information acquired simultaneously by each of the imaging elements. Such methods may include, for example, building a memory map based on a model of the pipe inspected. The memory map may be, for example, fixed or morphable, with respect to the size of the pipe.

In another aspect, the disclosure relates to a camera apparatus for in inspection operations such as inspecting piping or other cavities. The apparatus may include, for example, a camera head assembly. The camera head assembly may include a housing. The camera head assembly may include a plurality of imaging sensors disposed on or within the housing. The camera head assembly may include one or more electronic circuits for receiving image or video signals from one or more of the imaging sensors and generating an output signal. The camera head may include a communications circuit for sending the output signal to a display device or other coupled device.

In another aspect, the disclosure relates to a pipe inspection system. The pipe inspection system may include, for example, a push-cable. The pipe inspection system may further include a camera head assembly coupled to the push-cable. The camera head assembly may include a housing, a plurality of imaging sensors disposed in the housing, an electronic circuit for receiving image or video signals from one or more of the imaging sensors and generating an output signal, and a communications circuit for sending the output signal to a coupled device. The pipe inspection system may further include a camera control unit (CCU) coupled to the push-cable as the coupled device. The CCU may include a user interface device for controlling digital articulation of the camera head. The CCU may further include a display for providing a visual display based on a plurality of images or video stream captured by the imaging sensor or based on a plurality of images or video streams captured by ones of the plurality of image sensors. The coupled device may be a tablet, notebook computer, or cellular phone or electronic device. The coupled device may be coupled to the camera head via a wired connection, such as USB or other serial connection, Ethernet connection, or other wired connection. The coupled device may be coupled to the camera head via a wireless connection. The wireless connection may be a Wi-Fi connection or other wireless local area network connection.

In another aspect, the disclosure relates to a method for inspecting a pipe. The method may include, for example, capturing, in a first image sensor disposed in a camera head, a first image and capturing, in a second image sensor disposed in the camera head, a second image. The field of view (FOV) of the first image sensor may overlap the field of view of the second image sensor. The method may further include generating, such as in a processing element in the camera head or other device or system, based on the first image and the second image, an output image or signal corresponding to a digital articulation of the camera head. The output image or signal may be one or more images or a video stream. The output image may be based at least in part on the first image and the second image. The output image may be further based on one or more additional images from one or more of a plurality of image sensors in the camera head. The one or both of the first image and the second image may be adjusted to correct for optical distortion, noise, color, contrast, or other distortions or characteristics. The output image may include a portion of the first image and a portion of the second image that may be combined or stitched with the portion of the first image.

In another aspect, the disclosure relates to one or more computer readable media including non-transitory instructions for causing a computer to perform the above-described methods and/or system or device functions, in whole or in part.

In another aspect, the disclosure relates to apparatus and systems for implementing the above-described methods and/or system or device functions, in whole or in part.

In another aspect, the disclosure relates to means for implementing the above-described methods and/or system or device functions, in whole or in part.

Various additional aspects, features, and functionality are further described below in conjunction with the appended Drawings.

BRIEF DESCRIPTION OF THE DRAWINGS

The present disclosure may be more fully appreciated in connection with the following detailed description taken in conjunction with the accompanying drawings, wherein.

DETAILED DESCRIPTION

Overview

Figure 1:
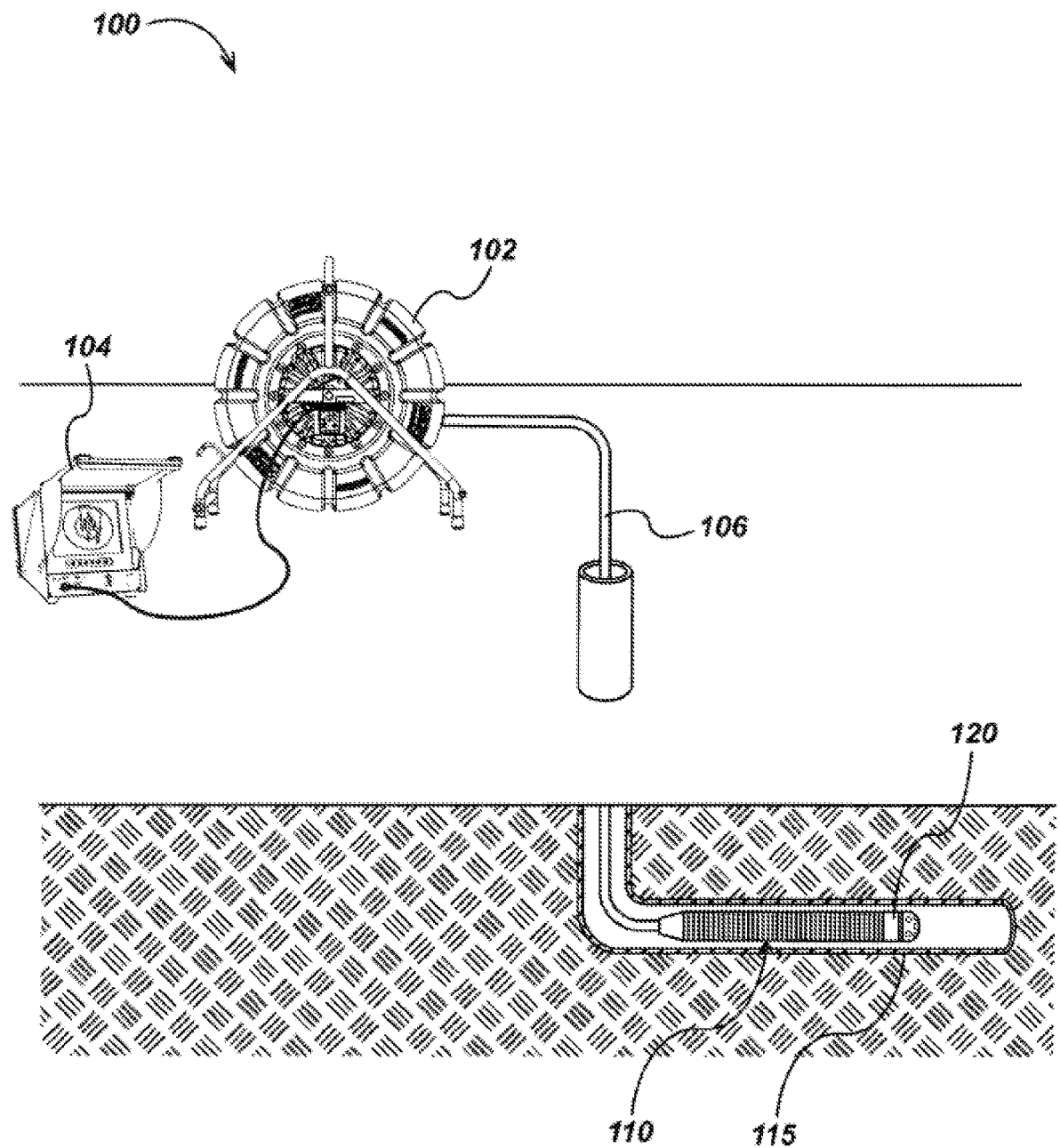
FIG. 1 illustrates details of a pipe inspection system configured with a multi-imager camera head.

This disclosure relates generally to apparatus, systems, and methods for visually inspecting the interior of pipes and other conduits or voids. More specifically, but not exclusively, the disclosure relates to apparatus and systems for providing images or video of the inside of a pipe based on data received from a plurality of imaging sensors.

For example, in one aspect, the disclosure relates to a camera head including an array of two or more imaging elements with overlapping Fields of View (FOV). The camera head may be fixedly or removably coupled to the end of a push-cable to allow inspect the interior of a pipe, conduit, and the like by being pushed into the pipe. The camera head may include one or more light source elements, such as LEDs for providing illumination in dimly lit inspection sites, such as the interior of underground pipes. The imaging elements and LEDs may be used in conjunction with a remote display device, such as an LCD panel or monitor in proximity to an operator, to display the interior of a pipe or other cavity. The display device may be part of a camera controller device or other display or data storage device, such as a notebook computer, tablet, smart phone, and the like.

In another aspect, the imaging elements and light source elements may be automatically controlled and/or manually controlled by the operator. For example, automatic control may be used to provide an image or video signal from one or more of the imaging elements based on an orientation of the camera within the pipe or cavity. Control signals may be provided from an orientation sensor such as an accelerometer or other orientation sensor. Manual control may be used to allow an operator to select one or more of the imaging elements and/or one or more of the LEDs for viewing the interior of the pipe or other cavity, such as by a switch, button, or other user input mechanism. The LEDs may be individually controlled, such as turning one or more LEDs on or off to reduce heat in the camera head. The LEDs may additionally be used individually to provide various shadow patterns, which may be useful for diagnosing an inspection area. Images or video acquired from the imaging elements may be processed to provide a 3-dimensional view of the interior of the pipe or other cavity. Images or video may be captured from multiple imaging sensors and processed in an electronic circuit of a camera apparatus, such as within a camera head, to generate an output signal including output images or video based on imaging data received from a plurality of the imaging sensors. The output signal may include a digitally synthesized articulation of the camera head based on data received by the plurality of imaging sensors.

In another aspect, the disclosure relates to image processing methods used in a multi-camera pipe inspection system. Such methods may include, for example, generating a new image based on the information acquired simultaneously by each of the imaging elements. Such methods may include, for example, building a memory map based on a model of the pipe inspected. The memory map may be, for example, fixed or morphable, with respect to the size of the pipe.

In another aspect, the disclosure relates to a camera apparatus for in inspection operations such as inspecting piping or other cavities. The apparatus may include, for example, a camera head assembly. The camera head assembly may include a housing. The camera head assembly may include a plurality of imaging sensors disposed on or within the housing. The camera head assembly may include one or more electronic circuits for receiving image or video signals from one or more of the imaging sensors and generating an output signal. The camera head may include a communications circuit for sending the output signal to a display device or other coupled device.

The imaging sensors may, for example, be disposed on or within the housing so as to provide overlapping fields of view (FOV). The electronic circuit may include one or more processing elements or other programmable circuits for generating the output signal as a composite of two or more images or a video stream based on signals provided by two or more of the imaging sensors. The output signal may include a plurality of image frames or a video stream corresponding to a digitally simulated articulation of the camera head across a field of view seen by two or more of the imaging sensors. The digitally simulated articulation may be automatically performed or may be performed in response to an articulation control signal provided by a camera control unit (CCU) or other communicatively coupled device or system.

The camera apparatus may, for example, further comprising one or more lighting elements disposed on or within the housing. The lighting elements may be LEDs or other lighting devices.

The camera apparatus may further include one or more orientation or position sensors disposed on or within the housing. The one or more orientation or position sensors may be coupled to the electronic circuit to provide information regarding an orientation of the camera apparatus. The output signal may be based in part on the provided orientation information. The orientation sensors may be one or more of a compass sensor, a gyroscopic sensor, and an accelerometer. The sensors may be single axis or multi-axis sensors, such as two or three-axis sensors. The camera apparatus may further include one or more acoustic sensors, such as microphones or other acoustic sensors, disposed in the housing. The camera apparatus may further include one or more temperature sensors disposed in the housing. Information from the sensors may be combined, displayed, and/or stored in a memory in association with the images or video stream.

The output image may, for example, be based at least in part on a first image provided from a first image sensor of the plurality of image sensors and a second image provided by a second image sensor of the plurality of image sensors. One or both of the first image and the second image may be adjusted to correct for optical distortion, noise, color, contrast, or other characteristics or distortions. The output image may include a portion of the first image and a portion of the second image stitched with the portion of the first image. The output image may include portions of additional images stitched together with the first and/or second image.

The output signal may, for example, be generated based in part on a digital articulation control signal received at the camera head. The digital articulation control signal may be provided from a camera control unit (CCU) or other communicatively coupled device such as a notebook computer, cellular phone, tablet, or other electronic computing device.

The output signal may comprise a plurality of images or a video stream corresponding to a digital articulation of the camera head. The output signal may be combined with or integrated with sensor data. The digital articulation may be implemented automatically and/or in response to a digital articulation control signal received from a a camera control unit (CCU) or other communicatively coupled device such as a notebook computer, cellular phone, tablet, or other electronic computing device.

In another aspect, the disclosure relates to a pipe inspection system. The pipe inspection system may include, for example, a push-cable. The pipe inspection system may further include a camera head assembly coupled to the push-cable. The camera head assembly may include a housing, a plurality of imaging sensors disposed in the housing, an electronic circuit for receiving image or video signals from one or more of the imaging sensors and generating an output signal, and a communications circuit for sending the output signal to a coupled device. The pipe inspection system may further include a camera control unit (CCU) coupled to the push-cable as the coupled device. The CCU may include a user interface device for controlling digital articulation of the camera head. The CCU may further include a display for providing a visual display based on a plurality of images or video stream captured by the imaging sensor or based on a plurality of images or video streams captured by ones of the plurality of image sensors. The coupled device may be a tablet, notebook computer, or cellular phone or electronic device. The coupled device may be coupled to the camera head via a wired connection, such as USB or other serial connection, Ethernet connection, or other wired connection. The coupled device may be coupled to the camera head via a wireless connection. The wireless connection may be a Wi-Fi connection or other wireless local area network connection.

In another aspect, the disclosure relates to a method for inspecting a pipe. The method may include, for example, capturing, in a first image sensor disposed in a camera head, a first image and capturing, in a second image sensor disposed in the camera head, a second image. The field of view (FOV) of the first image sensor may overlap the field of view of the second image sensor. The method may further include generating, such as in a processing element in the camera head or other device or system, based on the first image and the second image, an output image or signal corresponding to a digital articulation of the camera head. The output image or signal may be one or more images or a video stream. The output image may be based at least in part on the first image and the second image. The output image may be further based on one or more additional images from one or more of a plurality of image sensors in the camera head. The one or both of the first image and the second image may be adjusted to correct for optical distortion, noise, color, contrast, or other distortions or characteristics. The output image may include a portion of the first image and a portion of the second image that may be combined or stitched with the portion of the first image.

The method may, for example, further include generating a plurality of output image frames corresponding to a digitally simulated articulation of the camera head across a field of view seen by two or more of the image sensors. The method may further include providing a controlled lighting output from one or more lighting elements. The lighting elements may be LEDs or other lighting devices.

The method may, for example, further include providing orientation signals from one or more orientation sensors regarding an orientation of the camera apparatus and generating the output image or signal based at least in part on the orientation signals. The orientation sensors may include one or more of a compass sensor, a gyroscopic sensor, and an accelerometer.

The method may, for example, further include providing an acoustic signal from one or more acoustic sensors. The acoustic signal may be an audible or ultrasonic or infrasonic acoustic signal. The method may further include providing temperate, pressure, and/or humidity signals from one or sensors. The sensor signals may be combined, stored, displayed, and/or transmitted with the images or video stream.

In another aspect, the disclosure relates to one or more computer readable media including non-transitory instructions for causing a computer to perform the above-described methods and/or system or device functions, in whole or in part.

In another aspect, the disclosure relates to apparatus and systems for implementing the above-described methods and/or system or device functions, in whole or in part.

In another aspect, the disclosure relates to means for implementing the above-described methods and/or system or device functions, in whole or in part.

Various additional aspects, features, and functionality are further described below in conjunction with the appended Drawings.

It is noted that as used herein, the term, "exemplary" means "serving as an example, instance, or illustration." Any aspect, detail, function, implementation, and/or embodiment described herein as "exemplary" is not necessarily to be construed as preferred or advantageous over other aspects and/or embodiments.

Various aspects of a multi-imager pipe inspection system, apparatus, devices, configurations, and methods that may be used in conjunction with embodiments of the disclosure herein are described in co-assigned patents and patent applications including U.S. Pat. No. 5,939,679, filed Feb. 9, 1998, entitled Video Push Cable, U.S. Pat. No. 6,545,704, filed Jul. 7, 1999, entitled Video Pipe Inspection Distance Measuring System, U.S. Pat. No. 6,958,767, filed Jan. 31, 2002, entitled Video Pipe Inspection System Employing Non-Rotating Cable Storage Drum, U.S. Pat. No. 6,862,945, filed Oct. 22, 2002, entitled Camera Guide for Video Pipe Inspection System, U.S. patent application Ser. No. 10/858,628, filed Jun. 1, 2004, entitled Self-Leveling Camera Head, U.S. patent application Ser. No. 11/928,818, filed Oct. 30, 2007, entitled Pipe Mapping System, U.S. patent application Ser. No. 12/399,859, filed Mar. 6, 2009, entitled Pipe Inspection System with Selective Image Capture, U.S. patent application Ser. No. 12/766,742, filed Apr. 23, 2010, entitled Pipe Inspection Cable Counter and Overlay Management System, U.S. patent application Ser. No. 12/371,540, filed Feb. 13, 2009, entitled Push-Cable for Pipe Inspection System, U.S. patent application Ser. No. 12/704,808, filed Feb. 12, 2010, entitled Pipe Inspection System with Replaceable Cable Storage Drum, U.S. patent application Ser. No. 13/346,668, filed Jan. 9, 2012, entitled PORTABLE CAMERA CONTROLLER PLATFORM FOR USE WITH PIPE INSPECTION SYSTEM, U.S. patent application Ser. No. 13/073,919, filed Mar. 28, 2011, entitled Pipe Inspection System with Jetter Push-Cable, U.S. patent application Ser. No. 13/358,463, filed Jan. 25, 2012, entitled SELF-LEVELING INSPECTION SYSTEMS AND METHODS, U.S. Patent Application Ser. No. 61/559,107, filed Nov. 13, 2011, entitled PORTABLE PIPE INSPECTION SYSTEMS AND APPARATUS, U.S. Patent Application Ser. No. 61/592,524, filed Jan. 30, 2012, entitled ADJUSTABLE VARIABLE RESOLUTION INSPECTION SYSTEMS AND METHODS, U.S. Patent Application Ser. No. 61/602,065, filed Feb. 22, 2012, entitled DOCKABLE TRIPODAL CAMERA CONTROL UNIT, U.S. Patent Application Ser. No. 61/602,527, filed Feb. 23, 2012, entitled DOCKABLE TRIPODAL CAMERA CONTROL UNIT, U.S. Patent Application Ser. No. 61/602,063, filed Feb. 22, 2012, entitled THERMAL EXTRACTION ARCHITECTURE CAMERA HEADS & INSPECTION SYSTEMS, U.S. Patent Application Ser. No. 61/654,713, filed Jun. 1, 2012, entitled SYSTEMS AND METHODS INVOLVING A SMART CABLE STORAGE DRUM AND NETWORK NODE FOR TRANSMISSION OF DATA, and U.S. Patent Application Ser. No. 61/641,254, filed May 1, 2012, entitled HIGH BANDWIDTH PUSH-CABLES FOR VIDEO PIPE INSPECTION SYSTEMS. The content of each of these applications is hereby incorporated by reference herein in its entirety for all purposes.

Referring to FIG. 1, an example pipe inspection system 100, on which embodiments of the various aspects of the disclosure may be implemented, is illustrated. Pipe inspection system 100 may include an inspection assembly 110 coupled to the end of a push cable 106, which may be stored and fed into a conduit, such as pipe 105, from a reel 102. Reel 102 may be connected to an image display device 104 via a physical cable or wireless link.

Pipe inspection assembly 110 may include a camera apparatus including a camera head assembly 120, which may include one or more sensors for providing sensor data signals corresponding to one or more conditions of the camera head inside pipe 115, as well as analog or digital electronic circuits, optics, processing elements, and the like. For example, one or more imaging sensors (imagers), such as CMOS, CCD, or other imaging sensors, may be used to image areas being viewed and provide data signals corresponding to image or video streams captured within the pipe 115, and which may be processed in a processing element and/or display device to provide a visualization of the interior of the pipe as images or video presented on the display device 104. Display device 104 may be, for example, a camera controller or other display device, such as a notebook computer, tablet, smart phone, video monitor, and the like.

One or more orientation sensors (not shown), such as one or more three-axis compass sensors, one or more three-axis accelerometers, one or more three-axis gyroscopic ("gyro") sensors, and/or one or more inertial or other position, motion, or orientation sensors may be used to provide data signals corresponding to the orientation of the camera head, such as a relative up/down orientation with respect to the Earth's gravity and/or relative to other parameters such as the Earth's magnetic field. Gyros may be particularly useful if the earth's magnetic field is distorted by residual magnetism or adjacent ferromagnetic materials. A temperature sensor (not shown) may provide data signals corresponding to temperature, and acoustic sensors may provide data signals corresponding to sounds or ultrasonic or subsonic signals. Other sensors, such as temperature sensors, acoustic sensors, pressure sensors, and the like, may also be used to provide data signals corresponding to environmental or other operating conditions, such as temperature, pressure, sound, humidity, and the like.

Push-cable 106 may include electrical and/or optical conductors to provide output data signals from the camera head 110 to the display device 104 and provide electrical power to camera head assembly 120 from a power source (not shown). Push-cable 106 may be manually pushed down the length of pipe 115 by a user or through mechanical powering via an electrical motor or other mechanical or electromechanical apparatus.

The camera assembly 120 may further be configured with a jetter assembly as described, for example, U.S. patent application Ser. No. 13/073,919, filed Mar. 28, 2011, entitled "PIPE INSPECTION SYSTEM WITH JETTER PUSH-CABLE", to clear build-up, roots, and/or other obstructions or blockages found in pipe 105 or other cavity via high pressure. Alternately, or in addition, mechanical cutter heads or other cutting elements may also be coupled to the push cable to facilitate clearing of obstructions.

Figure 2:
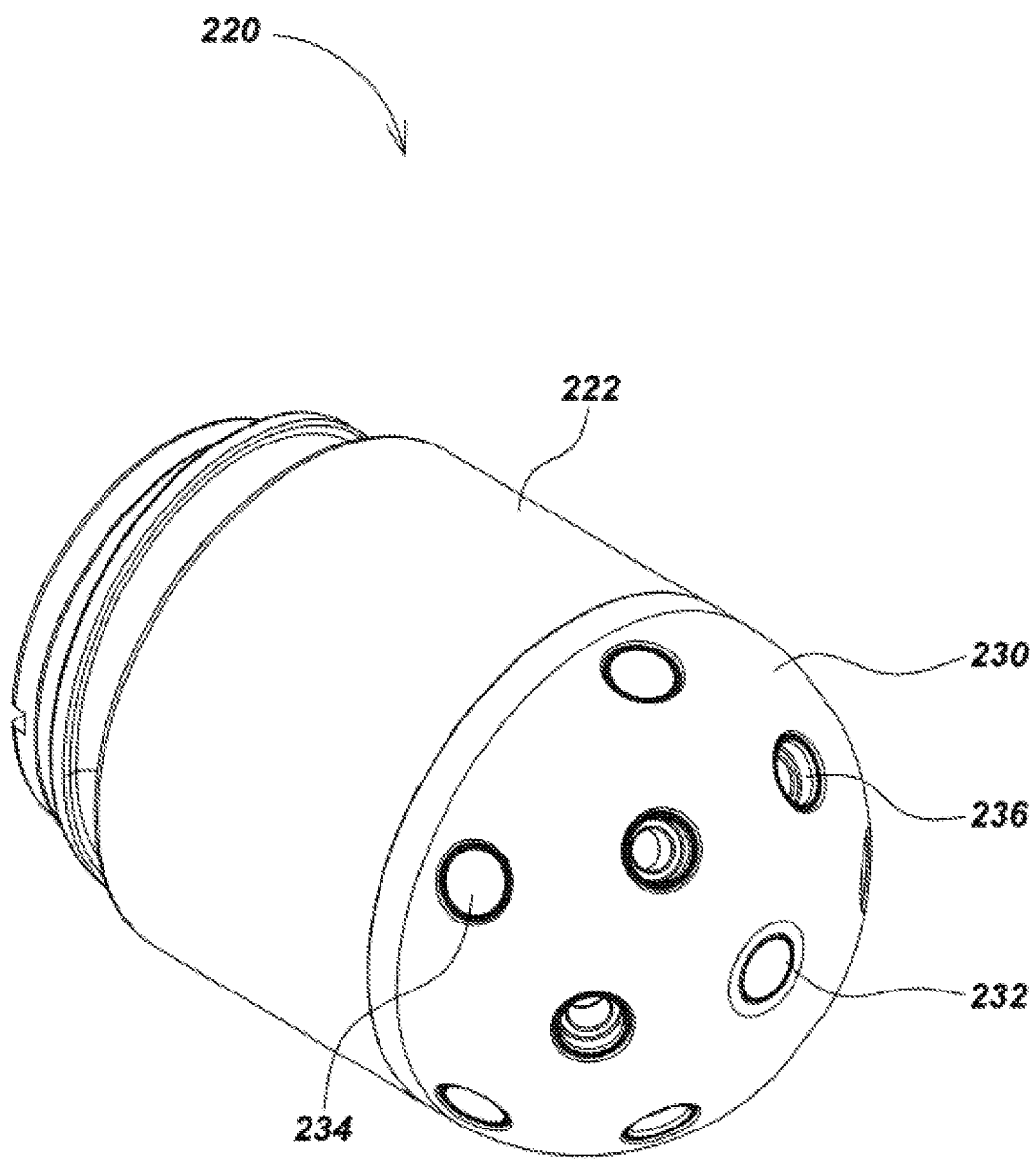
FIG. 2 illustrates details of an embodiment of a multi-imager camera head.

FIG. 2 illustrates details of a camera head assembly embodiment 220. Camera head assembly embodiment 220 may correspond with the camera head embodiment 120, as illustrated in FIG. 1. Camera head assembly 220 may include a rear camera housing 222 configured with a front camera housing 230. In other embodiments different numbers and/or configurations of elements may be used to form a camera housing structure. Front camera housing 230 may include a plurality of ports or apertures, which may be configured with one or more image sensors and/or one or more lighting elements. In an exemplary embodiment, one or more lighting elements, such as LEDs 236, and one or more image sensors 234 may be configured in one or more apertures in a concentric configuration. In one aspect, a central image sensor 232 having a field of view (FOV) (not shown), may be disposed at the front of camera head assembly 220 to provide image sensor data signal representing an FOV image or video stream. Image or video signals may be sent up the push-cable for real-time viewing, storage, presentation to the user, and/or transmission to other devices. In addition, still images may be sent when the camera head stops moving and/or both during motion or when stopped. In addition, other signals or information, such as sensor outputs, audio signals, or other data or information may be provided via conductors in the push-cable to a display device or other device or system for storage, presentation to a user, such as an a graphical user interface (GUI), or for transmission to other electronic computing systems or devices, such as cellular phones, tablets, notebook computers, and the like. The additional signals or information may be combined with the images or video streams for presentation to a user, such as on a display device such as an LCD panel and the like, and/or integrated with the images or video streams for storage and/or transmission to other devices. Examples of embodiments of imaging of areas being viewed and sending, displaying, storing, and transmitting corresponding images, video streams, and sensor data that may be combined in embodiments with the disclosure herein are described in, for example, co-assigned U.S. patent application Ser. No. 13/754,767, filed Jan. 30, 2013, entitled ADJUSTABLE VARIABLE RESOLUTION INSPECTION SYSTEMS AND METHODS, as well as U.S. patent application Ser. No. 13/774,351, filed Feb. 22, 2013, entitled DOCKABLE TRIPODAL CAMERA CONTROL UNIT. The content of each of these applications is incorporated by reference herein.

For example, various environmental condition sensor data or operating environment or other sensor data may be sent over suitable conductors (not shown) via push cable 106. In an exemplary embodiment, orientation sensors (not shown), such as one or more gyro sensors, one or more compass sensors, tilt sensors, and/or one or more one or more one dimensional (e.g., three dimensional) accelerometer sensors (not shown) for sensing the tilt/orientation of the camera head 220 and/or motion of the camera head, may be used to provide data signals corresponding to such conditions. These signals may be used by a processing element in the display device and/or camera head to adjust video or image data for relative orientation of the camera head with the pipe or other cavity. For example, an accelerometer may be disposed in the camera head 220 to sense motion and direction. The sensed information may be used to provide a top/bottom oriented output video or image signal. In addition, as soon as the camera head 220 stops moving, it may continue to display the center image (not shown) to the user on the screen of the display device 106 or may use motion or lack of motion to trigger events such as image capture or stoppage of capture. For example, when motion stops the camera head 220 may start sending each image, one after another to provide plurality of images, which may be stitched together in a processing element of a processing module as illustrated in systems 500 (FIG. 5) and 600 (FIG. 6), to provide a composite/panoramic image or video and/or a stereoscopic (3-D) image or video.

Figure 3:
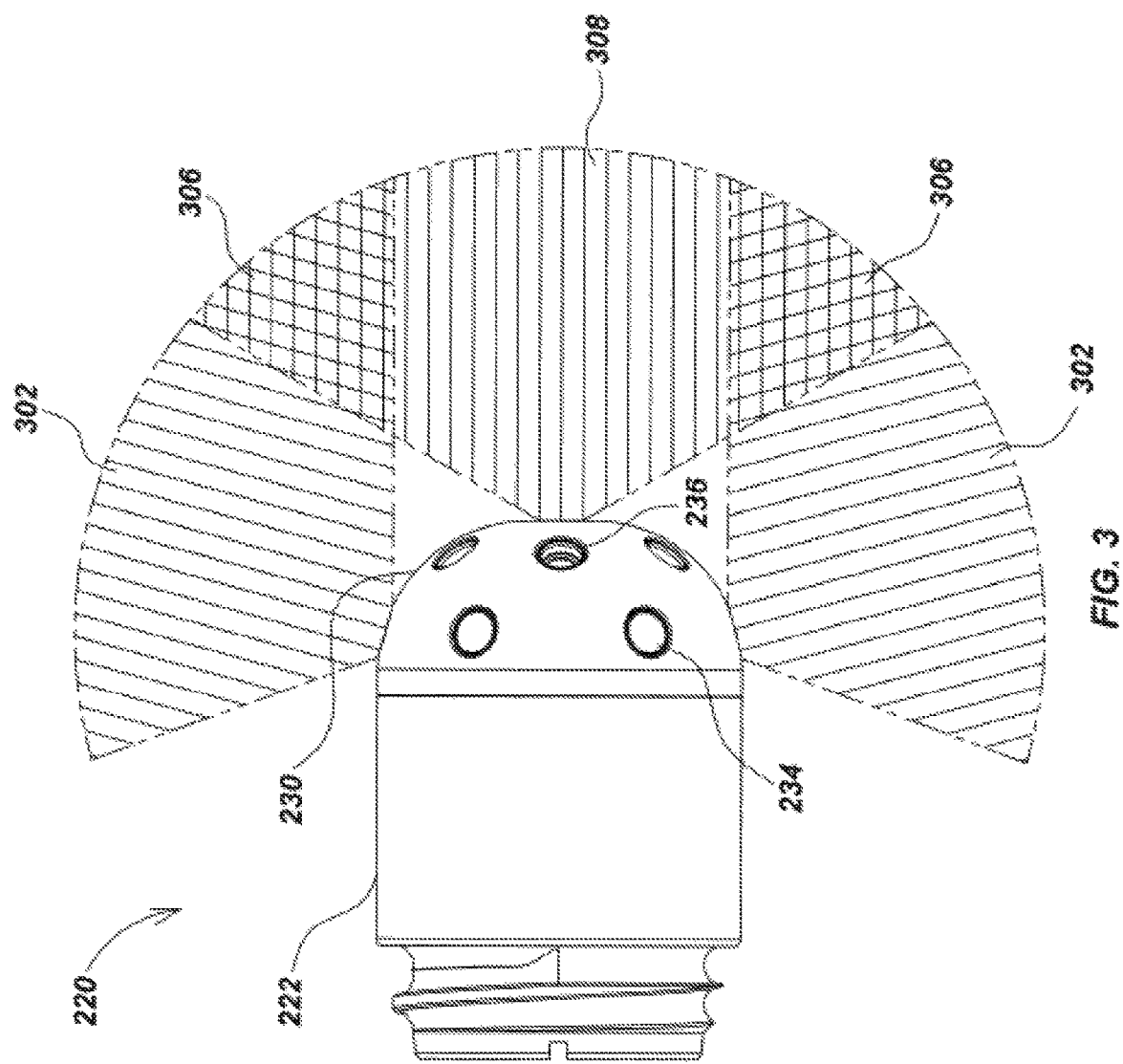
FIG. 3 is a side perspective view of the multi-imager camera head embodiment of FIG. 2, illustrating overlapping fields of view from adjacent imagers.

FIG. 3 is a side perspective view of the multi-imager camera head embodiment 220 of FIG. 2, illustrating overlapping fields of view from adjacent imagers. Central image sensor 232 (FIG. 2) may have a substantially vertical field of view (FOV), while image sensors 234 may have a substantially horizontal field of view 302. Vertical field of view and horizontal field of views may provide one or more overlapping fields of view 306.

Figure 4:
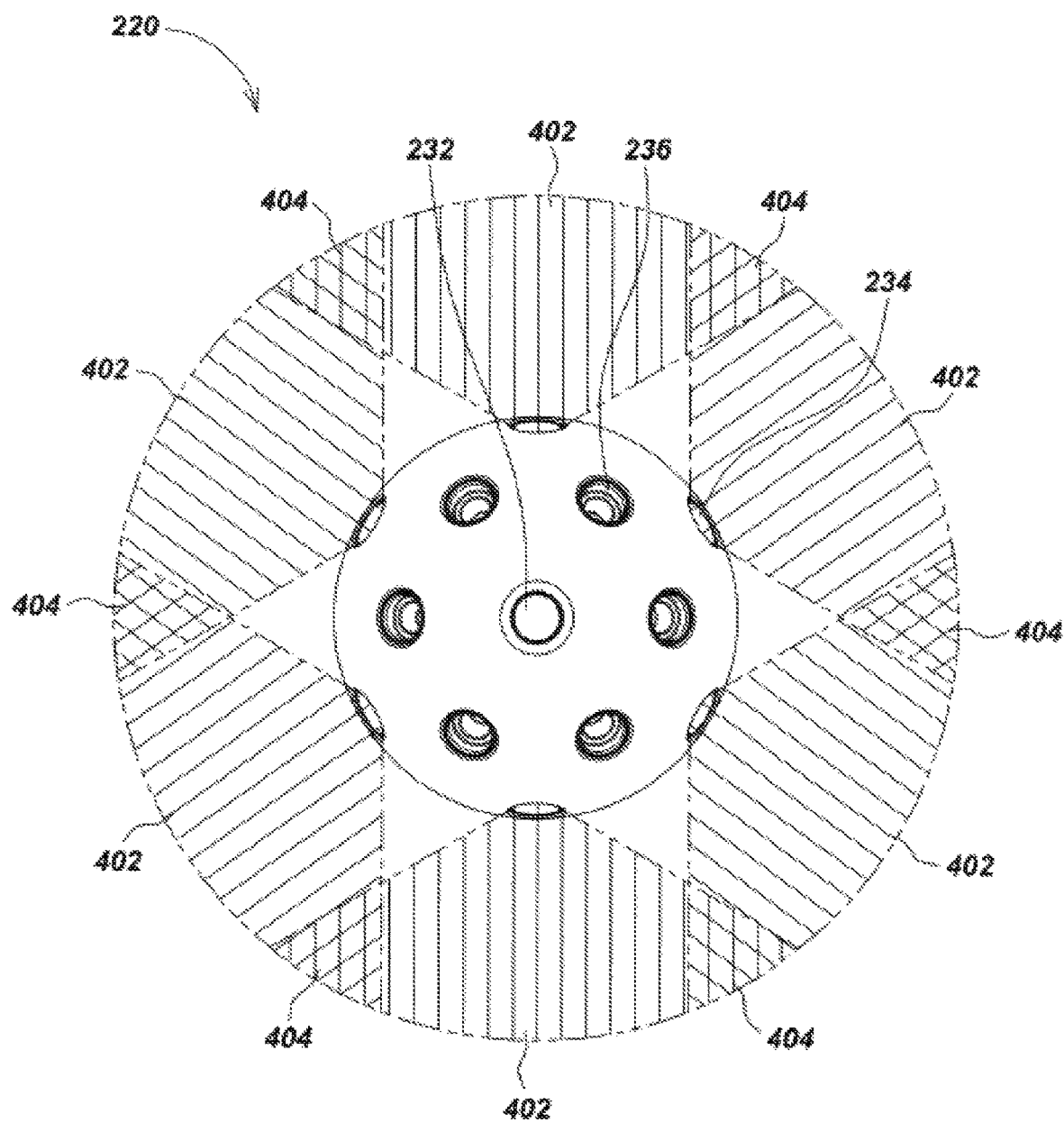
FIG. 4 is a front perspective view of the multi-imager camera head embodiment of FIG. 2, illustrating overlapping fields of view from adjacent imagers.

FIG. 4 is a front perspective view of the multi-imager camera head embodiment 220 of FIG. 2, illustrating overlapping fields of view from adjacent imagers. In one aspect, adjacent imager sensors 234 may provide fields of view, which may overlap with the fields of view of another image sensor to provide overlapping fields of view 404.

Figure 5:
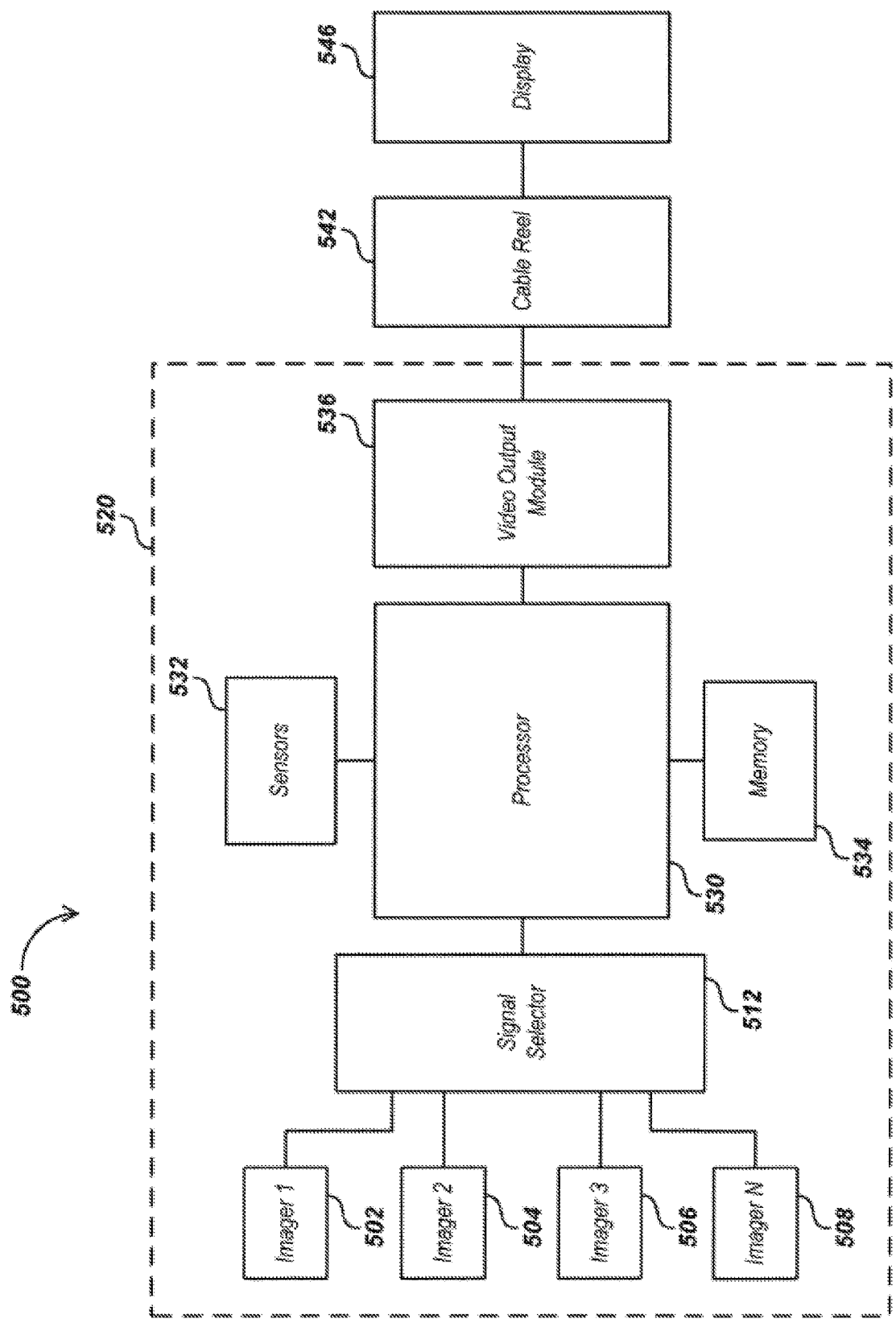
FIG. 5 is a block diagram illustrating details of an embodiment of a multi-imager pipe inspection system.

FIG. 5 is a block diagram illustrating details of an embodiment of a multi-imager pipe inspection system 500. In one aspect, various steps and processes may be carried out in a camera head module 520 and/or in a coupled device, such as a camera control unit (CCU) (not shown). In an exemplary embodiment, camera head module 520 may include a multiplexer (MUX) or signal selector 512, which may be used to increase the amount of data that can be sent over the network within a certain amount of time and bandwidth. For example, signal selector 512 may select and combine one or more analog or digital input information signals, such as, for example, image signals provided from imagers 502, 504, 506, and 508, and may forward the selected or combined input into a single output. In one aspect, a signal selector 512 may provide a single output to a processing module 530, which may be disposed in camera head module 520.

One or more sensors 532, such as orientation sensors, which may include one or more gyro sensors, one or more compass sensors, and/or one or more one or three-dimensional accelerometer sensors (not shown) for sensing the tilt/orientation of the camera head may be included to sense such conditions. Sensor information 532 and information stored in memory 534 may be sent to the processing module such that one or more images may be oriented properly and stitched together. Additional sensors, such as temperature sensors and acoustic sensors may be used to capture additional information, such as signals corresponding to temperature and sound, which may be later processed in the processing module 530.

Still referring to FIG. 5, the processor 530 may provide an output signal to a video output module 536, and the video output module 536 may supply a video signal to an image display device 546 via a cable reel 542. Cable reel 542 may include a push cable, such as push cable 106 of FIG. 1. The image display devices may be a display of a CCU or other device in communication with the camera head. Output images, video, sensor data, and/or other data or information may also be stored and/or transmitted to other communicatively coupled devices, such as notebook computers, cellular phones, tablet devices, and the like.

Figure 6:
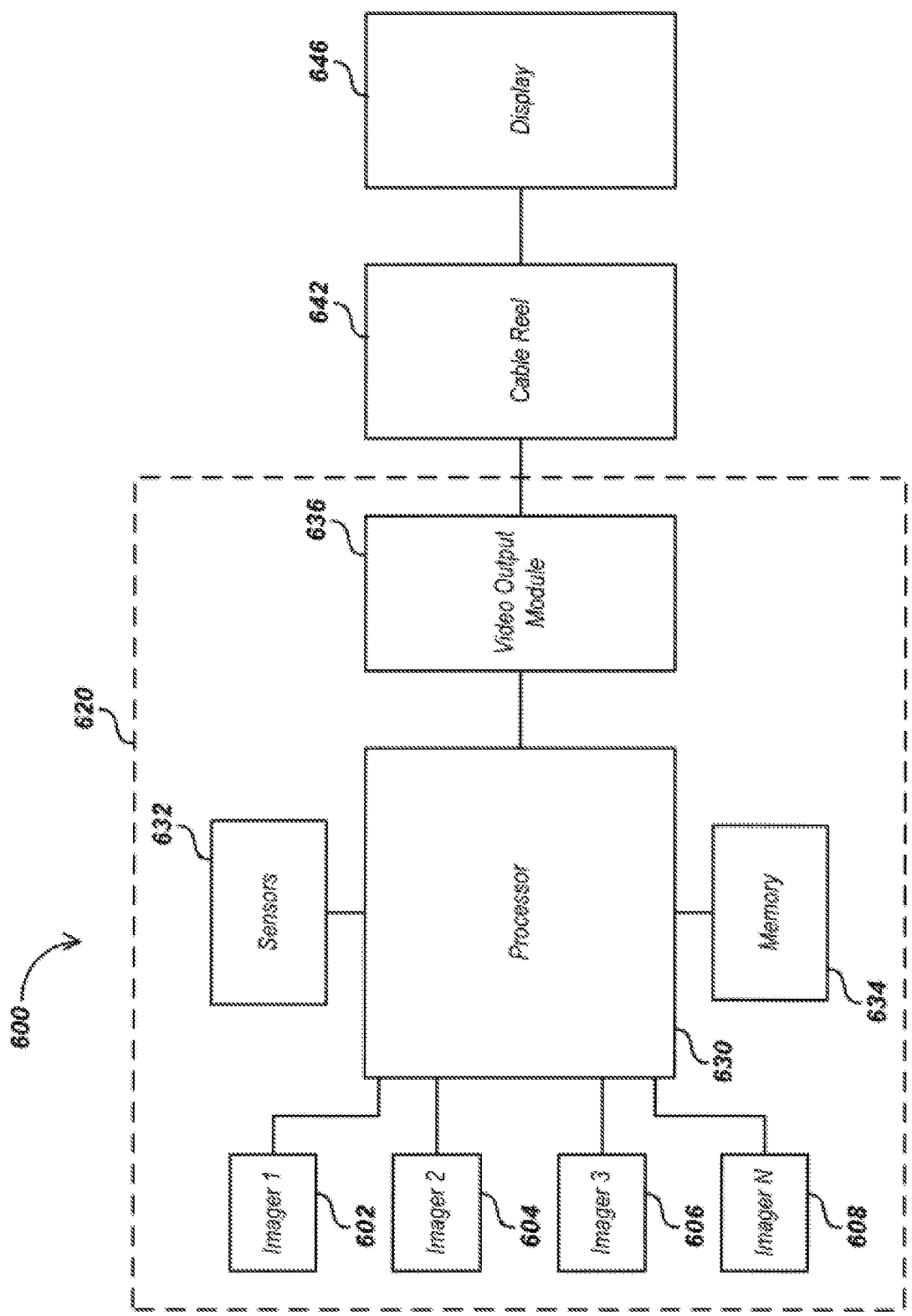
FIG. 6 is a block diagram illustrating details of an embodiment of a multi-imager pipe inspection system.

FIG. 6 is a block diagram illustrating details of an embodiment of a multi-imager pipe inspection system 600. In one aspect various steps and processes may be carried out in a camera head module 620. For example, one or more image signals provided from imagers 602, 604, 606, and 608, and may put input directly into a processing module 630. One or more sensors 632, such as orientation sensors, which may include one or more gyro sensors, one or more compass sensors, and/or one or more one or three-dimensional accelerometer sensors (not shown) for sensing the tilt/orientation of the camera head. Sensor information 632 and information stored in memory 634 may be sent to the processing module such that one or more images may be oriented properly and stitched together. Stitching of images may be done as described in, for example, U.S. Pat. No. 7,894,689, issued Feb. 22, 2011, entitled IMAGE STITCHING, U.S. Pat. No. 8,395,657, issued Mar. 12, 2013, entitled METHOD AND SYSTEM FOR STITCHING TWO OR MORE IMAGES, U.S. Pat. No. 7,609,626, issued Nov. 17, 2009, entitled MAPPING IMAGES FROM ONE OR MORE SOURCES INTO AN IMAGE FOR DISPLAY, U.S. Pat. No. 7,317,558, issued Jan. 8, 2008, entitled SYSTEM AND METHOD FOR PROCESSING MULTIPLE IMAGES, and/or from other image combining or stitching techniques known or developed in the art. The above-described patents are incorporated by reference herein. Additional sensors, such as temperature sensors and acoustic sensors may be used to capture additional information, such as signals corresponding to temperature and sound, which may be later processed in the processing module 630.

Still referring to FIG. 6, the processor 630 may provide an output signal to a video output module 636, and the video output module 636 may supply a video signal to an image display device 646 via a cable reel 642. Cable reel 642 may include a push cable, such as push cable 106 of FIG. 1. The image display devices may be a display of a CCU or other device in communication with the camera head. Output images, video, sensor data, and/or other data or information may also be stored and/or transmitted to other communicatively coupled devices, such as notebook computers, cellular phones, tablet devices, and the like.

Figure 7:
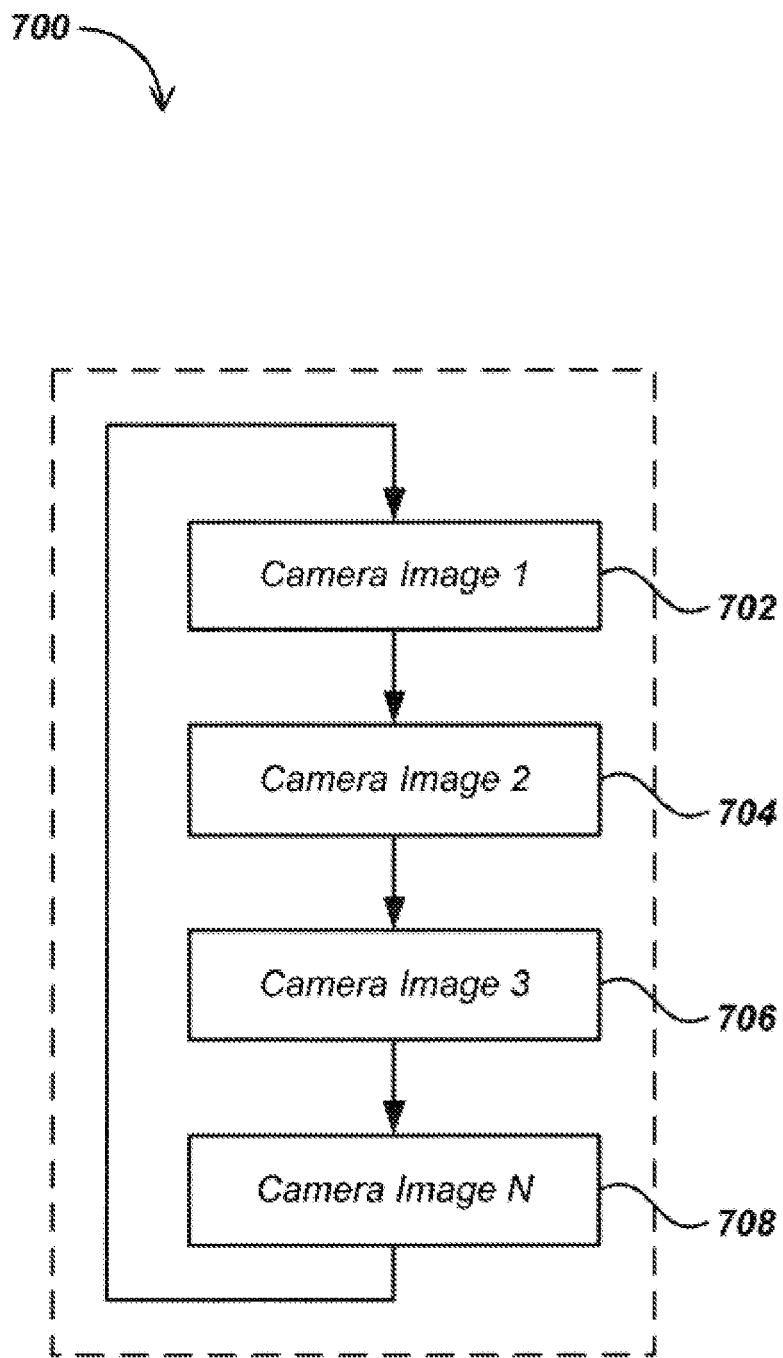
FIG. 7 is a flowchart illustrating processing details an embodiment of a multi-imager pipe inspection system.

FIG. 7 is a flowchart illustrating processing details an embodiment of a multi-imager pipe inspection system 700. For example, an orientation sensor, such as an accelerometer, senses the orientation, and the camera head, such as camera head 220 (FIGS. 2-4) sends images one after another (it sends a code to the CCU such that the CCU keeps displaying the one front image). For example, camera image 1 702, camera image 2 704, camera image 3 706, and camera image N 708, may each be sent one after another (as code) to the CCU such that the CCU keeps displaying the one front image.

Figure 8:
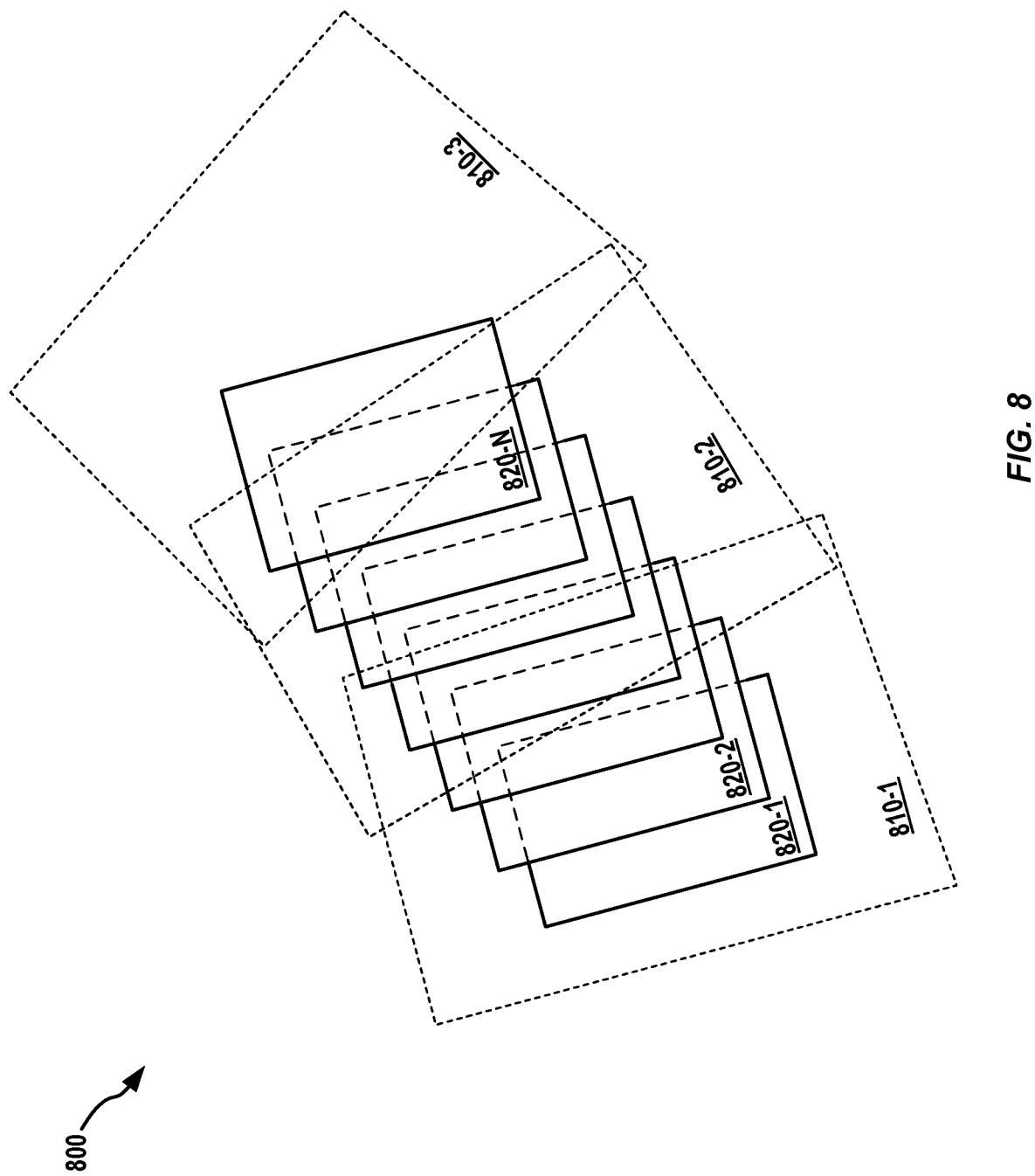
FIG. 8 illustrates an example processing sequence for generating a digitally articulated output image sequence or video signal.

FIG. 8 illustrates an example diagram 800 of image processing as may be done to provide a digitally synthesized articulated movement based on a plurality of images captured by a plurality of imaging sensors in a pipe inspection camera apparatus. An image sequence as shown in FIG. 8 may be provided in a series of images or in a video signal representing frames based on the series of images. Control of the particular direction, zoom level, angle, and/or speed of the digitally articulated imaging may be done through a user control input, such as in the form of an electronic or optical signal, provided from a camera control unit (CCU) or other control mechanism.

As shown in FIG. 8, a plurality of imaging sensors (in this example, three sensors) may capture images within FOVs 810-1, 810-2, and 810-3. These FOVs will typically overlap in imaging area with respect to the pipe or cavity under inspection, except at distances extremely close to the camera head, depending on the imaging sensor spacing and angle of coverage of the imaging sensors. A typical imaging sensor may cover a field of view of 90 to 120 degrees, however, more sensors may be used in embodiments with sensors covering shorter angles. Imaging sensors may be packed within a camera head to minimize distances between sensors as described subsequently herein with respect to FIG. 8.

Images may be captured by the imaging sensors and data representing all or a portion of the imaging areas (e.g., areas 810-1, 810-2, 810-3) may be stored in a memory within the camera head and/or may be processed in a processing element either in the camera head or in another element of the pipe inspection system such as a display device or camera controller. If the image information is processed in the camera controller or other device of the system, the imaging data may be sent from the camera head to the camera controller or other device, such as through conductors within the push-cable.

The processing element may receive the image data corresponding to the covered areas (e.g., 810-1, 810-2, 810-3) and may then adjust the data to correct for optical distortions, noise, or other problems, such as described in U.S. Pat. No. 7,529,424, issued May 5, 2009, entitled CORRECTION OF OPTICAL DISTORTION BY IMAGE PROCESSING, which is incorporated by reference herein, and/or by other methods known or developed in the art. The aggregate image data may then be stored in memory and/or stitched together or otherwise processed to facilitate generation of output image or video data. The output image or video data may represent a sequence of images 820 corresponding to a subset of the captured image area, which may be "moved" to correspond with the change in field of view caused by a mechanical movement of the camera head (without need for any actual mechanical movement). The particular movement direction, speed, angle, zoom level, etc., may be provided from a user through a mouse, joystick, or other user input device.

The output sequence may be generated based on a simulated movement (e.g., panning, rotation, translation, zoom-in, zoom-out) relative to the aggregate imaged area. For example, as shown in FIG. 8, a sequence of images 820-1, 820-1, . . . 820-N may be generated from the data representing image areas 810-1, 810-2, and 810-3 so as to simulate a mechanical movement or articulation of the camera across the area shown in FIG. 8. This processing may be either with the camera head fixed in position to generate purely digital articulation or may be done in conjunction with actual mechanical movement of the camera head to generate a hybrid mechanical and digital articulation in some embodiments.

Figure 9:
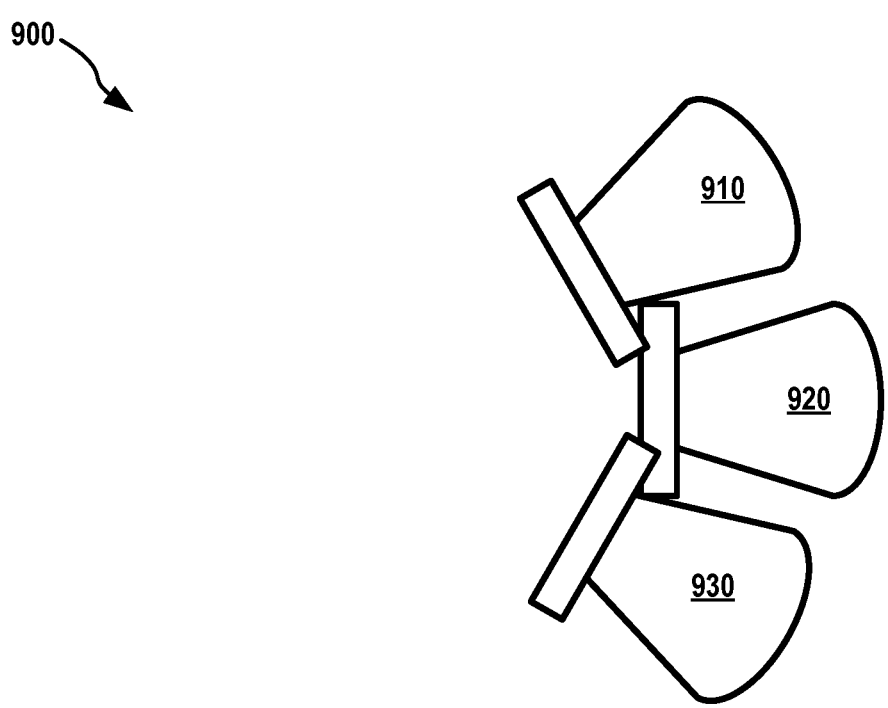
FIG. 9 illustrates an example imaging sensor packaging embodiment in a camera head assembly.

FIG. 9 illustrates details of an embodiment of tightly packed array 900 of imaging sensor assemblies (910, 920, and 930 as shown), which may include sensor chips, printed circuit boards, optics, and associated electronic and mechanical components. In array 900 only three imaging sensor assemblies are shown, however, in various embodiments additional imaging sensors in various sizes and configurations may be included. A plurality of imaging sensors may be arrayed in two or three dimensions in an imaging sensor array within a camera head as described previously herein. By packing the imaging sensor in such a configuration, the FOVs of the various sensors may be brought together and overlapped to provide the various functionality described previously herein.

Digital articulation actions may be implemented in a camera controller or other device using a mouse, joystick, or other user interface device. In an exemplary embodiment, a magnetically sensed user interface device as described in co-assigned applications of SeekTech, Inc., may be used to control digital and/or mechanical articulation actions.

In some embodiments, imaging data taken from two or more imaging devices may be used to determine internal distances in a pipe or other cavity by identifying features imaged on multiple sensors and using triangulation/trilateration to determine the distance based on know spacing between sensors, etc. In some embodiments, LEDs or other light emitting devices may be controlled in synchronization with the imaging sensors to control imaging functionality and to enhance signal processing. Multiple light illumination sources may be spaced between the imaging sensors to provide more controlled lighting.

In some embodiments, internal pipe or other cavity features may be reconstructed based on received stereoscopic images of a particular area of the pipe seen from different positions (e.g., different sensor spacing).

In various embodiments, one or more of the following functions may be implemented alone or in combination. For example, in general, articulated imaging based on digitally generated images may provide advantages in terms of fewer or no moving parts as would be needed for mechanical articulation of a camera head and associated components. Capturing and processing overlapping area of images allows stereo imaging and 3D reconstruction of internal pipe or other cavity geometry. Providing illumination in between lenses/imaging sensors may advantageously provide various advantages with respect to illumination of targeted areas as well as imaging of those areas. Use of near field imaging may be advantageous. In general, "Fly's Eye" multi-camera structures are designed to operate essentially in the far field (infinity) so that the degree of overlap is a very small function of distance. However, internal pipe and other closed quarter cavities may benefit in terms of overlap by using near field imaging and associated sensor and optics configurations.

Composite images may be assembled and processed in the camera head or the individual images may be captured locally and sent, via a communications connection such as a wired or wireless link to a remote processing device. A 3D mouse, such as described in Applicant's co-assigned applications, may be incorporated into a camera controller or other controlling device to control pan, tilt and zoom the composite images, such at by controlling digital image generation. Combining imaging with sensors (e.g. 9 axis motion/position sensors, etc.) may be used to provide mapping functionality by associating imaged information with location/position information, as well as to provide a "righting" function wherein captured images or video is orientation adjusted to present an upright view to a user and/or to store images or videos in an orientation adjusted way.

In some embodiments lighting may be strobed or otherwise controlled in a structured fashion, such as through use of spot lighting, infrared lighting, line-shaped lighting, grid lighting, circular lighting, etc. In some embodiments composite images may be captured when the camera head stops, such as capturing based upon sensors or a cable reel counter (e.g., when cable deployment reel counts slow down or stop). Composite images may be used to build a 3D model of the inside of the pipe.

Various camera array configurations may be used in various embodiments. For example, most or all of a central forward-looking area may be overlapped for mapping and/or stereoscopic, 3D processing. In some embodiments, the front camera housing can be metal with LED window. In other embodiments the front of the housing may be clear or transparent with camera windows. In this case, LEDs positioned internally to the housing may provide lighting in between shining through the transparent window.

In one or more exemplary embodiments, the electronic functions, methods and processes described herein and associated with imagers, processing elements, communication elements, and other pipe inspection system components may be implemented in hardware, software, firmware, or any combination thereof. If implemented in software, the functions may be stored on or encoded as one or more instructions or code on a computer-readable medium. Computer-readable media includes computer storage media. Storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

As used herein, computer program products comprising computer-readable media including all forms of computer-readable medium except, to the extent that such media is deemed to be non-statutory, transitory propagating signals.

It is understood that the specific order or hierarchy of steps or stages in the processes and methods disclosed herein are examples of exemplary approaches. Based upon design preferences, it is understood that the specific order or hierarchy of steps in the processes may be rearranged while remaining within the scope of the present disclosure unless noted otherwise.

Those of skill in the art would understand that information and signals, such as video and/or audio signals or data, control signals, or other signals or data may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, electro-mechanical components, or combinations thereof. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative functions and circuits described in connection with the embodiments disclosed herein with respect to camera and lighting elements may be implemented or performed in one or more processing elements of a processing module with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps or stages of a method, process or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

The scope of this disclosure is not intended to be limited to the aspects shown herein, but is to be accorded the full scope consistent with the specification and drawings, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c.

The previous description of the disclosed aspects is provided to enable any person skilled in the art to make or use the present disclosure. Various modifications to these aspects will be readily apparent to those skilled in the art, and the generic principles defined herein may be applied to other aspects without departing from the spirit or scope of the invention. Thus, the presently claimed invention is not intended to be limited to the aspects shown herein but is to be accorded the widest scope consistent with the appended Claims and their equivalents.

We claim:

1. A camera system for inspecting small pipes, comprising:
   a camera head assembly including:
      a compact waterproof housing comprising:
         a metallic dome shaped front housing element of a first diameter and having a plurality of non-overlapping apertures disposed therein, the non-overlapping apertures having diameters less than the first diameter divided by the number of apertures; and
         a cylindrical-shaped rear housing element mechanically coupled to the front housing element with a waterproof seal;
      a plurality of video imaging sensors disposed inside the housing behind ones of the plurality of apertures, wherein each video imaging sensor is fixedly positioned within the housing to cover a field of view that at least partially overlaps with the field of view of at least another one of the plurality of video imaging sensors, and wherein each video imaging sensor simultaneously captures and provides its own video imaging sensor video output signal corresponding to its covered field of view;
      an electronic circuit for receiving each of the video imaging sensor video output signals and generating a composite video output signal based on the simultaneously captured video imaging sensor video output signals of two or more of the plurality of video imaging sensors; and
      a wireless link for receiving the composite video output signal from the electronic circuit and wirelessly sending the composite video output signal to a communicatively coupled device.

2. The camera system of claim 1, wherein the composite video output signal includes a digitally simulated articulation of the camera head across a field of view seen by two or more of the imaging sensors while the camera head is maintained in a fixed position.

3. The camera system of claim 1, further comprising one or more LED lighting elements disposed on or within the housing in ones of the plurality of apertures so at to illuminate at least a portion of the aggregate fields of view of the imaging sensors.

4. The camera system of claim 1, further comprising one or more orientation sensors disposed within the housing, wherein the one or more orientation sensors are coupled to the electronic circuit to provide information regarding an orientation of the camera head assembly.

5. The camera system of claim 4, wherein the orientation sensors comprise one or more of a compass sensor, a gyroscopic sensor, and an accelerometer.

6. The camera system of claim 5, further comprising one or more acoustic sensors disposed in the housing.

7. The camera system of claim 6, further comprising one or more temperature sensors disposed in the housing.

8. The camera system of claim 1, wherein the composite video output signal is based at least in part on a first of the video imaging sensor output signals provided from a first video imaging image sensor of the plurality of video imaging sensors and a second video imaging sensor output signal provided by a second video imaging sensor of the plurality of video imaging sensors, and wherein one or both of the first video imaging sensor and the second video imaging sensor output signals are adjusted to correct for optical distortion of video imaging sensor optics.

9. The camera system of claim 2, wherein the output signal is generated based in part on a digital articulation control signal provided from a camera control unit (CCU) or wirelessly coupled device and received at the camera head.

10. A camera system for inspecting pipes or cavities, comprising:
- a camera head assembly including:
  - a compact waterproof housing comprising:
    - a metallic dome shaped front housing element of a first diameter and having a plurality of non-overlapping apertures disposed therein, the non-overlapping apertures having diameters less than the first diameter divided by the number of apertures; and
    - a cylindrical-shaped rear housing element mechanically coupled to the front housing element with a waterproof seal;
  - a plurality of video imaging sensors disposed inside the housing behind ones of the plurality of apertures, wherein each video imaging sensor is fixedly positioned within the housing to cover a field of view that at least partially overlaps with the field of view of at least another of the plurality of video imaging sensors, and wherein each video imaging sensor simultaneously captures and provides its own video imaging sensor video output signal corresponding to its covered field of view;
- an electronic circuit for receiving the video imaging sensor video output signals and generating a composite video output signal based on the video imaging sensor video output signals of two or more of the plurality of video imaging sensors; and
- a display device operatively coupled to the electronic circuit for receiving the composite video output signal and rendering the composite video output signal thereon.

* * * * *